US007354711B2

(12) United States Patent
Macfarlane (10) Patent No.: US 7,354,711 B2
(45) Date of Patent: Apr. 8, 2008

(54) METHODS FOR INHIBITING IMMUNOSTIMULATORY DNA ASSOCIATED RESPONSES

(75) Inventor: Donald E. Macfarlane, Iowa City, IA (US)

(73) Assignees: University of Iowa Research Foundation, Iowa City, IA (US); The Department of Veterans Affairs, as represented by the Secretary of United States of America, Washington, DC (US)

( * ) Notice: Subject to any disclaimer, the term of this patent is extended or adjusted under 35 U.S.C. 154(b) by 692 days.

(21) Appl. No.: 10/336,635

(22) Filed: Jan. 3, 2003

(65) Prior Publication Data

US 2003/0232856 A1    Dec. 18, 2003

Related U.S. Application Data

(62) Division of application No. 10/115,421, filed on Apr. 2, 2002, now Pat. No. 6,521,637, which is a division of application No. 09/768,874, filed on Jan. 23, 2001, now Pat. No. 6,399,630, which is a division of application No. 09/109,513, filed on Jul. 2, 1998, now Pat. No. 6,221,882.

(60) Provisional application No. 60/051,666, filed on Jul. 3, 1997.

(51) Int. Cl.
*C12Q 1/68* (2006.01)
*C08K 5/16* (2006.01)
(52) U.S. Cl. .......................................... 435/6; 524/187
(58) Field of Classification Search ................ 435/5–6, 435/7.2
See application file for complete search history.

(56) References Cited

U.S. PATENT DOCUMENTS

| | | | | |
|---|---|---|---|---|
| 2,233,970 | A | 3/1941 | Andersag et al. ............ | 260/288 |
| 5,583,153 | A | 12/1996 | Brahn .......................... | 513/449 |
| 5,641,868 | A * | 6/1997 | Sakurai et al. .............. | 530/412 |
| 6,207,646 | B1 * | 3/2001 | Krieg et al. .................. | 514/44 |
| 6,225,292 | B1 * | 5/2001 | Raz et al. ..................... | 514/44 |

OTHER PUBLICATIONS

Yi et al. CpG DNA rescue of murine B lymphoma cells from anti-IgM induced growth arrest and programmed cell death is associated with increased expression of c-myc and bcl-xl The Journal of Immunology, Dec. 1, 1996, vol. 157, 4918-4925.*
Manzel et al. CpG-Oligodeoxynucleotide supports growth of IL-6 dependent 7TD1 murine hybridoma cells. Life Sciences, published Nov. 1997, vol. 62, No. 1, 23-27.*
Klinman et al. CpG motifs present in bacterial DNA rapidly induce lymphocytes to secrete interleukin 6, interleukin 12, and interferon gamma. Proc. Natl. Acad. Sci. USA, Apr. 1996, vol. 93, 2879-2883.*
Raz et al. U.S. Appl. No. 60/048,793.*
Chou et al., "Surrogate models for antimalarials," In: *Antimalarial Drugs*, Peters and Richard (eds.), Springer Verlag Berlin, 1974, p. 281-329.
Corcoran et al., "Mechanism of action of antimicrobial and antitumor agents," In: *Antibiotics III*, Springer Verlag, Berlin, 1975, p. 59-78.
Elslager et al., "Antimalarial and antischistosomal effects of proximal hydrazine and hydroxylamine analogs of chloroquine and quinacrine," *J. Org. Chem.*, 12:970-974, 1969.
Elslager et al., "Repository drugs. 8. Ester and amide congeners of amodiaquine, hydroxychloroquine, oxychloroquine, primaquine, quinacrine, and related substances as potential long-acting antimalarial agents," *J. Org. Chem.*, 12:600-607, 1969.
Ferrante et al., "Depression of human polymorphonuclear leucocyte function by anti-malarial drugs" *Immunology*, 58:125-130, 1986.
Foldes-Filep et al., "Mepacrine inhibits fMLP-induced activation of human neutrophil granulocytes, leukotrinene $B_4$ formation, and fMLP binding," *J. Leuk. Biol.*, 52:545-550, 1992.
Hannun, "Functions of ceramide in corrdinating cellular responses to stress," *Science*, 274:1855-1859, 1996.
Hurst et al., "Differential effects of mepacrine, chloroquine and hydroxychloroquine on superoxide anion generation, phospholipid methylation and arachidonic acid release by human blood monocytes," *Biochem. Pharmacol.*, 35:3083-3089, 1986.
Jakobsen et al., "The antimalarial drug, Ro 42-1611 (arteflene), does not affect cytoadherence and cytokine-inducing properties of plasmodium falciparum malaria parasites," *Trop. Med. Parasitol.*, 46(2):88-92, 1995.
Krakauer, "A sensitive, specific immunobioassay for quantification of human interleukin 6," *J. Immunoassay*, 14:267-277, 1993.
Macfarlane and Manzel, "Antagonism of immunostimulatory CpG-oligodeoxynucleotides by quinacrine, chloroquine, and structurally related compounds," *J. Immunology*, 160:1122-1131, 1998.
MacFarlane et al., "Unmethylated CpG-containing oligodeoxynucleotides inhibit apoptosis in WEHI 231 B lymphocytes induced by several agents: evidence for blockade of apoptosis at a distal signalling step," *Immunology*, 91:586-593, 1997.
Manzel et al., "CpG-oligodeoxynucleotide supports growth of IL-6-dependent 7TD1 murine hybridoma cells," *Life Science*, 62:23-27, 1998.
Marquez et al., "Mechanism of ation of amoidoquine synthesis of its indoloquinoline analog," *J. Med. Chem.*, 15:36-39, 1972.

(Continued)

*Primary Examiner*—Bruce Campell
*Assistant Examiner*—Emily M. Le
(74) *Attorney, Agent, or Firm*—Wolf, Greenfield & Sacks, P.C.

(57) ABSTRACT

The invention features methods for inhibiting immunostimulatory DNA-associated immune responses, through the administration of specific compounds of the general class of 9-aminoacridines and 4-aminoquiniolines. The invention also features methods of screening compounds useful in inhibiting immunostimulatory DNA-induced immune responses.

4 Claims, 6 Drawing Sheets

OTHER PUBLICATIONS

Mattsson et al., "Intracellular pathways involved in tumor necrosis factor-alpha release by human monocytes on stimulation with lipopolysaccharide or staphylococcal peptidoglycan are partly similar," *Joint Infectious Diseases*, 173:212-218, 1996.

Papadopoulos et al., "Bioassay vs. immunoassay for quantification of interleukin-6 in biological fluids," *J. Clin. Lab Anal.*, 9:234-237, 1995.

Roberts et al., "The regulation of neutrophil phosphoipase $A_2$ by granulocyte-macrophage colony-stimulating factor and its role in priming superoxide production," *Brit. J. Haematol.*, 92: 804-814, 1996.

Sakuta et al., "Inhibition of SKF 525A and quinacrine of endogenous glibenclamide-sensitive K channels in follicle-enclosed Xenopus ocytes," *Eur. J. Pharmacol.*, 252:117-121, 1993.

Tamamizu et al., "Mutations in the M1 region of the nicotinic acetylcholing receptor alter the sensitivity to inhibition by Quinacrine," *Cell. Mol. Neurobiol.*, 15:427-438, 1995.

\* cited by examiner

METHODS FOR INHIBITING IMMUNOSTIMULATORY DNA ASSOCIATED RESPONSES

This is a divisional of U.S. application Ser. No. 10/115,421, filed Apr. 2, 2002, now U.S. Pat. No. 6,521,637, issued on Feb. 18, 2003, which is a divisional of U.S. application Ser. No. 09/768,874, filed Jan. 23, 2001, now U.S. Pat. No. 6,399,630 issued on Jun. 4, 2002; which is a divisional of U.S. patent application Ser. No. 09/109,513, filed Jul. 2, 1998, now U.S. Pat. No. 6,221,882 issued on Apr. 24, 2001, which claims priority to provisional application Ser. No. 60/051,666, filed Jul. 3, 1997, now expired, each of which are incorporated by reference.

This invention was made in the performance of a Cooperative Research and Development Agreement with the Department of Army, U.S. Army Medical Research and Material Command DAMD17-97-0097. The invention may be manufactured and used by the Government of the United States for all governmental purposes without any payment or any royalty.

BACKGROUND OF THE INVENTION

The invention relates to a method of inhibiting cellular and humoral responses to immunostimulatory DNA with compositions including 4-aminoquinolines, 9-aminoacridines and derivatives thereof.

Bacterial DNA is increasingly recognized as a powerful modulator of immunity (Krieg, 1997. *Trends in Microbiol.* 4:73-6), stimulating the polyclonal proliferation of B-cells and the production of cytokines by monocytes and other cells (Ballas et al., 1996. *J. Immunol.* 157:1840-5). This activity is attributed to unmethylated CpG sequences in bacterial DNA, which are uncommon in vertebrate DNA (Krieg et al., 1995. *Nature* 374:546-9). Single stranded oligodeoxynucleotides which have the motif PuPuCGPyPy (CpG-ODN) mimic many of the actions of bacterial DNA (Krieg et al., 1996. *Antisense & Nucleic Acid Drug Devel.* 6:133-9), and powerfully inhibit the induction of apoptosis in mouse WEHI 231 B-cells by anti-surface IgM (Yi et al., 1996. *J. Immunol.* 157:4918-25; Macfarlane et al., 1997. *Immunology* 91:586-593). This system is a convenient and reproducible model to study responses to immunostimulatory DNA.

Bacterial DNA immobilized on beads does not stimulate immune responses, suggesting that internalization of the DNA is required for activity DNA and oligodeoxynucleotides are endocytosed into acidic vesicles, and are then transported to the cytoplasm and nucleus of cells.

Chloroquine, hydroxychloroquine and quinacrine are known to induce remissions of systemic lupus erythematosus and rheumatoid arthritis by an unknown mechanism. These drugs bind to DNA by intercalation. They are weak bases and partition into acidic vesicles. At high concentrations, chloroquine can collapse the pH gradient and disrupt the action of endosomal hydrolytic enzymes and the trafficking of receptors.

SUMMARY OF THE INVENTION

The invention is based on the discovery that quinacrine, chloroquine and selected 9-aminoacridine and 4-aminoquinoline compounds unexpectedly block the action of immunostimulatory DNA in cells at concentrations much below those needed for the other immunomodulatory effects of these compounds in vitro. The 9-aminoacridine and 4-aminoquinoline compounds utilized in the methods of the invention inhibit the anti-apoptotic effect of CpG-ODN and the CpG-ODN-induced secretion of IL-6. On the other hand, these compounds do not influence the anti-apoptotic effects of other agents, for example, lipopolysaccharides. The effects of the compounds are highly specific to immunostimulatory DNA. These agents are useful for inducing remissions of autoimmune disorders such as rheumatoid arthritis and systemic lupus erythematosus, leading to generally useful remittive and anti-inflammatory agents.

The methods of the invention are useful for inhibiting immunostimulatory DNA-associated responses in a subject, and involve the administration of a composition to a subject exhibiting responses initiated or exacerbated by immunostimulatory DNA. The compositions include 4-aminoquinolines, 9-aminoacridines and derivatives thereof. These compounds may be linked to each other by linkers. The responses initiated or exacerbated by immunostimulatory DNA include those which result in the initiation or exacerbation of various disease states. The disease states include septic shock, inflammatory bowel diseases, asthma, sinusitis, various autoimmune disorders such as hemolytic anemia, and others. The responses to be inhibited include the production of immunomodulatory proteins such as cytokines, interleukins, interferons, cell growth factors and chemokines. One such protein is IL-6. Other responses to be inhibited by the methods of the invention are high levels of erythrocyte sedimentation, and high levels of immunoglobulin.

The invention also features a method of screening compounds useful for inhibiting immunostimulatory DNA-associated responses. This method involves contacting a cell with immunostimulatory DNA, thereby inducing a measurable immune response, and a test compound. Any inhibition of the immune response is detected. The cells can be hybridoma plasma cells, including 7TD1.

A "nucleic acid" or "DNA" means multiple nucleotides (i.e., molecules comprising a sugar (e.g., ribose or deoxyribose)) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the term refers to ribonucleotides as well as oligodeoxynucleotides. The term also includes polynucleosides (i.e., a polynucleotide minus the phosphate) and any other organic base-containing polymer. Nucleic acid molecules can be obtained from existing nucleic acid sources (e.g., genomic or cDNA), but are preferably synthetic (e.g., produced by oligonucleotide synthesis). A "stabilized nucleic acid molecule" or "nuclease-resistant nucleic acid molecule" means a nucleic acid molecule that is relatively resistant to in vivo degradation (e.g., via an exo- or endo-nuclease). Stabilization can be a function of length or secondary structure. Unmethylated CpG-containing nucleic acid molecules that are tens to hundreds of kilobases long are relatively resistant to in vivo degradation. For shorter immunostimulatory nucleic acid molecules, secondary structure can stabilize and increase their effect. For example, if the 3' end of a nucleic acid molecule is self-complementary to an upstream region, so that it can fold back and form a stem loop structure, then the nucleic acid molecule becomes stabilized and therefore exhibits more activity.

Preferred stabilized or nuclease-resistant nucleic acid molecules referred to in the instant invention have a modified backbone. For use in immune stimulation especially preferred stabilized nucleic acid molecules are phosphorothioate-modified nucleic acid molecules (i.e., at least one of the phosphate oxygens of the nucleic acid molecule is replaced by sulfur). Preferably the phosphate modification occurs at or near the 5' and/or 3' end of the nucleic acid molecule. In addition to stabilizing nucleic acid molecules, phosphorothioate-modified nucleic acid molecules (including phosphorodithioate-modified) can increase the extent of immune stimulation of the nucleic acid molecule, which contains an unmethylated CpG dinucleotide.

International Patent Application Number WO 95/26204 entitled "Immune Stimulation by Phosphorothioate Oligonucleotide Analogs" also reports on the non-specific immunostimulatory effect of phosphorothioate modified oligonucleotides. International Patent Application WO 96/02555 discloses the ability of unmethylated CpG-containing oligonucleotides to activate lymphocytes. Unmethylated CpG-containing nucleic acid molecules having a phosphorothioate backbone have been found to preferentially activate B-cell activity, while unmethylated CpG-containing nucleic acid molecules having a phosphodiester backbone have been found to preferentially activate monocytic (macrophages, dendritic cells and monocytes) and NK (natural killer) cells. Other stabilized nucleic acid molecules include non-ionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Nucleic acid molecules that contain a diol, such as tetraethyleneglycol or hexaethyleneglycol, at either or both termini have also been shown substantially resistant to nuclease degradation.

As used herein, the term "immunostimulatory DNA" refers to bacterial DNA, viral DNA, other DNA, synthetic double- or single-stranded DNA, DNA synthesized with a nuclease-resistant backbone or at least a partially nuclease resistant backbone, (such as a phosphorothioate-backboned DNA) which stimulates (e.g., has a mitogenic effect on, or induces or increases cytokine expression by vertebrate lymphocytes. Such immunostimulatory DNA includes that which contains an unmethylated cytosine, guanine (CpG) dinucleotide sequence. A "CpG" or "CpG motif" refers to a nucleic acid having cytosine followed by a guanine linked by link containing phosphorus. The term "methylated CpG" refers to the methylation of the cytosine on the pyrimidine ring, usually occurring at the 5'-position of the pyrimidine ring. The term "unmethylated CpG" refers to the absence of methylation of the cytosine on the pyrimidine ring. Methylation, partial removal, or removal of an unmethylated CpG motif in an oligonucleotide of the invention is believed to reduce its effect. Methylation or removal of all unmethylated CpG motifs in an oligonucleotide substantially reduces its effect. The effect of methylation or removal of a CpG motif is "substantial" if the effect is similar to that of an oligonucleotide that does not contain a CpG motif.

As used herein, the term "airway obstruction" includes respiratory ailments such as asthma, sinusitis, as well as airway obstructions caused by an infection, or exacerbated by an infection.

The terms "lower alkyl" and "lower alkoxy" refer to alkyl- and alkoxy groups comprising up to 7 carbon atoms. The terms include straight and branched chain groups. The term "alicylic" refers to a non-aromatic carbon chain system forming a ring, and having from 4 to 10 members. The term "polyalicyclic" refers to a non-aromatic carbon chain system forming more than one ring each ring having from 4 to 10 members. The term "aryl group" refers to aromatic hydrocarbons having from 6 to 26 carbons.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods and examples are illustrative only and not intended to be limiting.

DETAILED DESCRIPTION

Unexpectedly we find that compounds quinacrine, chloroquine, and other structurally related 4-aminoquinolines and 9-aminoacridines are extremely potent inhibitors of the action of immunostimulatory DNA. These compounds added in low nanomolar concentrations, completely block the ability of immunostimulatory DNA to protect WEHI 231 cells from growth arrest, DNA fragmentation and inhibition of thymidine incorporation induced by the engagement of its surface IgM, as well as apoptosis induced by other agents such as lipopolysaccharides. The inhibitory effect is non-competitive with respect to CpG-ODN, and it occurs even when quinacrine is added after the immunostimulatory DNA. The potency of chloroquine, quinacrine and derivatives is magnified by inhibition of the multi-drug resistance pump, suggesting that their site of action is intracellular. The specificity of the effect toward CpG-ODN is illustrated by the fact that quinacrine does not influence the ability of lipopolysaccharides (LPS) to inhibit apoptosis in WVEHI 231 cells. These results can be reviewed in light of the known biological effects in vitro of quinacrine and chloroquine.

Being a diprotic weak base, chloroquine (and many of the other compounds which were used) partitions into the acidified cellular vesicles, such as lysosomes. At high concentration, chloroquine can collapse the pH gradient of lysosomes and induce their swelling. The compounds chloroquine, hydroxychloroquine and quinacrine induce remissions of rheumatoid arthritis and systemic lupus erythematosus. The beneficial effect of these compounds becomes apparent over the course of several weeks. To account for this valuable therapeutic action, a number of investigators have explored the effects of the compounds on immune and inflammatory responses in vitro, revealing a wide range of inhibitory actions. Quinacrine inhibits phospholipase A2 (Roberts el al., 1996. *British J. Haematology* 92:804-14), blocks ion channels (Sakuta et al., 1994. *Eur. J. Pharm.* 252:117-21), binds to receptors (Tamamizu et al., 1995. *Cell. & Mol. Neurobiol.* 15:427-38), and inhibits fMLP-induced superoxide production and enzyme release by granulocytes (Foldes-Filep et al., 1992. *J. Leuk. Biol.* 52:545-50). Chloroquine and quinacrine have little influence on other functional assays of neutrophils (Ferrante et al., 1986. *Immunol.* 58:125-30). Chloroquine inhibits cytokine release from mononuclear cells induced by endo- and exo-toxins (Mattson et al., 1996. *J. Infect. Dis.* 173:212-8). Each of these described effects requires concentrations of chloroquine or quinacrine markedly higher than the concentrations used in the present invention to inhibit CpG-ODN-driven responses in WEHI 231 cells, and none of them satisfactorily explains the remittive effect of these drugs on autoimmune disorders. Chloroquine delays the recycling of proteins to the cell surface from lysosomes, resulting in altered trafficking of lysosomal enzymes and receptors (Chou et al., 1974 in *Antibiotics III. Mechanism of action of antimicrobial and antitumor agents* (Corcoran, J., and Hahn, F., eds.), pp. 281-92, Springer Verlag, Berlin). These effects on lysosomal functions are seen only when cells are exposed to higher concentrations of chloroquine than used here, so it is improbable that the suppression by the compounds of CpG-ODN responses can be attributed solely to these relatively gross actions, even though experiments with ammonia plus bafilomycin $A_1$ suggest that the immunostimulatory DNA-associated response requires vesicular acidification.

Methods of Inhibiting Immunostimulatory DNA-induced Responses

The invention features methods for inhibiting immunostimulatory DNA-induced responses in a subject. This method includes the administration of a therapeutically effective amount of a composition to the subject. The composition contains a compound that is effective in inhibiting immunostimulatory DNA-induced responses.

Compounds found to be useful for inhibiting immunostimulatory DNA-associated responses include 4-aminoquinoline compounds of the formula $R_A$ can be a hydrogen atom, a lower alkyl group, or can be further linked to $R_B$ by an alkyl chain. If $R_A$ is a lower alkyl group, it is preferred to be methyl or ethyl. If $R_A$ is further linked to $R_B$ by an alkyl chain (in addition to the depicted linkage by the nitrogen atom), the alkyl chain can be —$(CH_2)_n$—, where n is from 4 to 7, and is preferably 4 or 5.

The substituent $R_B$ can be a hydrogen atom, an alicyclic group (such as a cyclopentyl, cyclohexyl or cycloheptyl group), an alkyl secondary, tertiary or quaternary amino group or alkenyl secondary, tertiary or quaternary amino group. For example, $R_B$ can be an unsubstituted alkyl amine, such as 4-[pentyl-N,N-dialkyl amine], 4-[pentyl-N-alkyl amine], 4-[pentyl amine], 4-[butyl-N,N-dialkyl amine], 4-[butyl-N-alkyl amine], 4-[butyl amine], 2-[ethyl-N,N-dialkyl amine], 2-[ethyl-N-alkyl amine], 2-[ethyl amine], 3-[propyl-N,N-dialkyl amine], 3-[propyl-N-alkyl amine], and 7-[hepta-4-methyl-4-azaamine]. The N-substituents are generally lower alkyl, but can also include hydroxy-substituted lower alkyl, such as 2-hydroxyethyl. Unsaturated chains include 4-[pent-2-enyl-N,N-dialkyl amine] and 4-[pent-2-enyl-N-alkyl amine]. Longer amine-containing alkyl chains can also be utilized, and the nitrogen need not be located at the terminus of the substituent group. Cyclic amines can be included in the alkyl chain. For example, the alkyl chain can terminate in, or be interrupted by, a pyrrole ring, a piperazidyl ring, a piperidyl ring, or a morpholinyl ring, any of which may be further substituted with lower alkyl groups. In embodiments in which $R_B$ is an unsubstituted amine-containing group, the preferred variants of $R_B$ can be 2-[ethyl-N,N-dimethyl amine], 2-[ethyl-N-methyl amine], 4-[pentyl-N,N-diethyl amine], and 4-[butyl-N,N-diethyl amine].

The $R_B$ amine-containing chains described above can be variously substituted. Substituents include lower alkyl groups, such as methyl, ethyl and propyl. Other useful $R_B$ substituents include substituted or unsubstituted aryl groups, such as phenyl, anisyl, hydroxyphenyl, chlorophenyl, dichlorophenyl, fluorophenyl, naphthyl, thiophenyl, which can be substituted at o-, m- or p-positions, or at 1- or 2-positions in case of naphthyl; heterocyclic groups, such as pyridyl, pyrrolyl, piperidyl, and piperazidyl; or halogen, such as chloro, bromo, and fluoro; and other substituents such as hydroxyl, and alkoxyl. Further substitution of this amine-containing alkyl chain can comprise, for example, amide or ester linkages, ether or thioether linkages. The amine-containing alkyl chain can terminate with a substituent group such as a primary, secondary or tertiary amine, a hydroxy group, a thiol, a carboxylic acid, or an amide.

$R_B$ can also be a alipolycyclic group, such as bicycloheptyl, bicyclooctyl, or adamantyl, and can be linked to any position of these groups. $R_B$ can also be linked to $R_A$ by an alkyl chain.

The substituent $R_2$ can be a hydrogen atom, a lower alkyl group, or an aryl group. $R_2$ can also be a heteroaromatic group, such as 2-, 3-, or 4-pyridyl, 1-, 2-, or 3-pyrrolyl, or an aryl substituted lower alkenyl group, such as trans-β-styryl and trans-β-[α,β-trans-dimethyl-p-chlorostyryl]. It is believed that bulky groups at $R_2$ contribute to the efficacy of the compounds of the invention. Thus, many of the embodiments include bulky groups at this position. Among the unsubstituted aryl groups useful as $R_2$ substituents include phenyl, 1- and 2-naphthyl, 1-. 2-, 3-, 4-, or 9-phenanthryl and the like. Among the substituted aromatic hydrocarbons include the above-mentioned aryl groups, substituted with lower alkyl groups such as methyl and ethyl; halogens, such as chlorine, fluorine and bromine; perfluoroalkyl groups such as trifluoromethyl and pentafluoroethyl; alkoxy groups, such as methoxy; aryloxy groups such as phenoxy; amine-containing substituents such as N-[ N,N-dimethyl ethylene-diamine], or 1-[4-methylpiperazine]. Any of the above groups can be present at o-, m-, or p-positions on a phenyl ring, or at any synthetically feasible position on another aryl system. Multiply substituted aryl rings are also possible.

The substituent $R_3$ can be a hydrogen atom, a lower alkyl group such as methyl or ethyl, or an aromatic group such as phenyl. In certain preferred embodiments, the substituent $R_3$ is hydrogen or methyl.

The substituent $R_5$ can be a hydrogen atom, a lower alkyl group such as methyl or ethyl, or a halogen atom, such as chlorine, bromine or fluorine.

The substituent $R_6$ can be a hydrogen atom, a lower alkyl group such as methyl or ethyl, a lower alkoxy group such as methoxy or ethoxy, an aryloxy group such as phenoxy, an aryl group such as phenyl, an amine group such as N,N-dimethyl amino or N,N-diethylamino, or a thioether group such as phenylthioether or benzylthioether. It is found that bulky substituents on position 6 of the quinoline ring tend to enhance activity, so that many of the preferred embodiments include bulky groups at this position.

The substituent $R_7$ can be a hydrogen atom, a lower alkyl group such as methyl or ethyl, a lower alkoxy group such as methoxy or ethoxy, an aryloxy group such as phenoxy, a halogen atom such as chlorine, bromine or fluorine, or a lower haloalkyl group, namely a lower perfluoroalkyl group, such as trifluromethyl or pentafluoroethyl.

The substituent $R_8$ can be a hydrogen atom or a lower alkoxy group such as methoxy or ethoxy. Pharmaceutically acceptable salts of any of these compounds are also included in the invention. These salts include protonated or deprotonated atoms on the 4-aminoquinoline and counterions including potassium, sodium, chlorine, bromine, acetate and many other commonly recognized counterions.

If $R_7$ is a halogen, then at least one of $R_2$, $R_3$, $R_5$, $R_6$, or $R_8$ is not a hydrogen atom and $R_B$ is not 4-[(N,N-dialkyl-n-pentylamine] or 4-[N-alkyl-N-hydroxyalkyl-n-pentylamine].

It is further found that the 4-aminoquinoline compounds which inhibit immunostimulatory DNA-associated responses can be linked together via a linker. The linker can be connected to each molecule at either the same position on the compound, or at different positions. Preferred linked 4-aminoquinoline compounds are linked at the same position on each compound. The preferred position for linkage between the individual 4-aminoquinoline compounds is at the 4-amino position, shown as $R_A$ or $R_B$ in the structure. The linker can be of a number of types. Preferred linker types are alkyl chains, alkyl chains interrupted with nitrogen atoms, or alkyl chains interrupted with amide linkages. The alkyl chains are preferred to be at least two carbons in length and not more than twelve carbons in length. If the alkyl chain is interrupted by nitrogen atoms, it is preferred that the overall length of the chain be between two and twelve atoms. Preferred linker molecules include those of the formula —[(CH$_2$)$_{n1}$N(R)(CH$_2$)$_{n2}$]$_{n3}$—where n1, n2 and n3 are independently between 1 and 5, and R is a hydrogen atom, a carbonyl group or a lower alkyl group. The linker can further include substituents to vary the hydrophobicity or hydrophilicity of the linked compound as a whole.

Further compounds found to be useful for inhibiting immunostimulatory DNA-associated responses include 9-aminoacridine compounds of the formula The substituent $R_B$ can be a hydrogen atom or an alkyl secondary, tertiary or quater-nary amino group. For example, $R_B$ can be an unsubstituted alkyl amine, such as 4-[pentyl-N,N-dialkyl amine], 4-[pentyl-N-alkyl amine], 4-[pentyl amine], 4-[butyl-N,N-dialkyl amine], 4-[butyl-N-alkyl amine], 4-[butyl amine], 2-[ethyl-N,N-dialkyl amine], 2-[ethyl-N-alkyl amine], 2-[ethyl amine], 3-[propyl-N,N-dialkyl amine], 3-[propyl-N-alkyl amine], and 7-[hepta-4-methyl-4-azaamine]. The N-substituents are generally lower alkyl, but can also include hydroxy-substituted lower alkyl, such as 2-hydroxyethyl. Unsaturated chains include 4-[pent-2-enyl-N,N-dialkyl amine] and 4-[pent-2-enyl-N-alkyl amine]. Longer amine-containing alkyl chains are also possible, and the nitrogen need not be located at the terminus of the substituent group. Cyclic amines can be included in the alkyl chain. For example, the alkyl chain can terminate in, or be interrupted by, a pyrrole ring, a piperazidyl ring, a piperidyl ring, or a morpholinyl ring, any of which may be further substituted with lower alkyl groups. In embodiments in which $R_B$ is an unsubstituted amine-containing croup, the preferred variants of $R_B$ are 2-[ N,N-dimethyl ethylamine], 2-[N-methyl ethylamine], 4-[N,N-diethyl pentylamine], and 4-[N,N-diethyl butylamine]. Preferred embodiments of the 9-aminoacridines useful in the invention have $R_B$ as 4-[4-aryl-N,N-dialkyl butylamine], 4-[4-heteroaromatic-N,N-dialkyl butylamine], 4-[4-aryl-N-alkyl butylamine], and 4-[4-heteroaromatic-N-alkyl bittylamine]. Quaternary nitrogen-containing variants of these residues are also envisioned as useful in the invention.

The $R_B$ amine-containing chains described above can be variously substituted. Substituents include lower alkyl groups, such as methyl, ethyl and propyl. Other useful $R_B$ substituents include substituted or unsubstituted aryl groups, such as phenyl, anisyl, hydroxyphenyl, chlorophenyl, dichlorophenyl, fluorophenyl, naphthyl, thiophenyl, which can be substituted at o-, m- or p-positions, or at 1- or 2-positions in case of naphthyl; heterocyclic groups, such as pyridyl, pyrrolyl, piperidyl, and piperazidyl; or halogen, such as chloro, bromo, and fluoro; and other substituents such as hydroxyl, and alkoxyl. Further substitution of this amine-containing alkyl chain can comprise, for example, amide or ester linkages, ether or thioether linkages. The amine-containing alkyl chain can terminate with a substituent group such as a primary, secondary or tertiary amine, an hydroxy group, a thiol, a carboxylic acid, or an amide. Preferred embodiments have 4-[N,N-dialkyl pentylamine], 4-[4-aryl-N,N-dialkyl butylamine] or 4-[4-heteroaromatic-N,N-dialkyl butylamine] groups at this position, in which the aryl or heteroaromatic group is unsubstituted or substituted by halogen or alkoxy, and the N,N-dialkyl groups are N,N-diethyl groups.

The substituent $R_2$ is a lower alkyl group, such as methyl or ethyl. Preferred embodiments have methyl at this position.

The substituent $R_3$ can be a hydrogen atom, or a lower alkoxy group

The substituent X is a halogen atom, such as chlorine, bromine or fluorine. Preferred embodiments have chlorine at this position.

It is further found that the 9-aminoacridine compounds which inhibit immunostimulatory DNA-associated responses can be linked together via a linker. The linker can be connected to each molecule at either the same position on the compound, or on different positions. Preferred linked 9-aminoacridine compounds are linked at the same position on each compound. The preferred position for linkage between the individual 9-aminoacridine compounds is at the 9-amino position, shown as $R_A$ or $R_B$ in the structure. The linker can be of a number of types. Preferred linker types are alkyl chains, alkyl chains interrupted with nitrogen atoms, or alkyl chains interrupted with amide linkages. The alkyl chains are preferred to be at least two carbons in length and not more than twelve carbons in length. If the alkyl chain is interrupted by nitrogen atoms, it is preferred that the overall length of the chain be between two and twelve atoms. Preferred linker molecules include those of the formula —$[(CH_2)_{n1}N(R)(CH_2)_{n2}]_{n3}$— where n1, n2 and to n3 are independently between 1 and 5, and R is a hydrogen atom, a carbonyl group or a lower alkyl group.

Further useful compounds for inhibiting immunostimulatory DNA-associated responses include 4-aminoquinoline compounds and 9-aminoacridine compounds linked together by a linker. Preferred linked 4-aminoquinoline/9-aminoacridine compounds are linked at analogous positions on each compound. The preferred position for linkage for the 9-aminoacridine compounds is at the 9-amino position, shown as $R_A$ or $R_B$ in the structure and the linker is further linked to the 4-amino position of the 4-aminoquinoline compound. The linker can be of a number of types. Preferred linker types are those discussed above in connection with the 4-aminoquinoline and 9-aminoacridine compounds.

The compositions used in the methods of the present invention are useful to inhibit cellular and humoral immune responses. Such immune responses can be associated with infections. These immune responses are associated with immunostimulatory DNA, and can result in disease states or can exacerbate disease states. The immune responses which are inhibited by the present methods include those associated with septic shock; inflammatory responses such as inflammatory bowel disease; respiratory tract infections such as asthma and sinusitis; autoimmune diseases such as rheumatoid arthritis, systemic lupus erythemetosus; and autoimmune diseases involving humoral immune responses, such as hemolytic anemia.

The immunostimulatory DNA-induced responses to be inhibited by the compounds discussed herein can lead to production of cytokines such as IL-6. Thus, the methods of the present invention are intended to inhibit production of IL-6 in cells. If subjects have circulating levels of IL-6 which exceed 20 picograms/milliliter, the subject can be a candidate for treatment with the methods of the invention. Normal circulating levels of IL-6 are approximately 10 picograms/milliliter, while circulating levels of subjects with systemic lupus erythemetosus (50 picograms/milliliter), cancer (70 picograms/milliliter), and septic shock (100 picograms/milliliter) are generally much higher (Papadapoulos 1995. *J. Clin. Lab. Anal.* 9:234-7). Thus the methods of the present invention will be useful for subjects exhibiting immunostimulatory DNA-induced disorders, and having circulating levels of IL-6 of at least 20 picograms/milliliter. Preferably, the subjects will have at least 40 picograms/milliliter of circulating IL-6.

The concentration of compounds included in compositions used in the methods of the invention can range from about 10 nM to about 10 μM, preferably about 10 nM to about 1 μM. Most preferably, the compounds are found in concentrations of from about 10 nM to about 100 nM.

The immunostimulatory DNA-induced responses to be inhibited by the compounds discussed herein can lead to an increase in gammaglobulin over the normal values found in subjects. Immunoglobulins can be measured by the nephelometric method, or by electrophoresis (both described in "Protein Abnormalities", by Stephan Ritzman, Alan Riss, 1982). For example, the normal gammaglobulin levels according to the nephelometric method are: IgG, 700-1500 milligrams/100 milliliters; IgA 70-400 milligrams/100 milliliters; IgM 30-300 milligrams/100 milliliters; and IgD 0-40 milligrams 100 milliliters. When measured by electrophoresis, the normal value for gammaglobulin is 0.7 to 1.5 milligrams/100 milliliters.

The immunostimulatory DNA-induced responses to be inhibited by the compounds discussed herein can lead to an increase in the erythrocyte sedimentation rate, as measured by the Westergren sedimentation rate determination (*Internal Medicine* vol. 1, Jay H. Stein, ed., 1983. Little Brown Co. p. 162). Normal sedimentation rates are up to 20 mm/hour, so that the methods of the invention can be used with subjects exhibiting Westergren erythrocyte sedimentation rates of more than 24 mm/hour.

"Administering" the pharmaceutical composition of the present invention can be accomplished by various means known to the skilled artisan. The pharmaceutical compositions according to the invention can be administered locally or systemically. The term "therapeutically effective amount" means the quantity of a compound according to the invention necessary to inhibit a symptom in a subject. A "subject" is any vertebrate animal, preferably a mammal, including humans. Amounts effective for therapeutic use will, of course, depend on the severity of the disease and the weight and general state of the subject. Typically, dosages used in vitro can provide useful guidance in the amounts useful for in situ administration of the pharmaceutical composition. Animal models well known to those of skill in the art can be used to determine effective dosages for treatment of particular disorders. Various considerations are described, e.g., in Gilman et al., eds., *Goodman and Gilman's: The Pharmacological Bases of Therapeutics*, 8th ed., Pergamon Press, 1990; and *Remington's Pharmaceutical Sciences*, 17th ed., Mack Publishing Co Easton, Pa., 1990, each of which is herein incorporated by reference.

The pharmaceutical compositions according to the invention are in general administered topically, intravenously, orally, or parenterally, or as implants, and even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solublizers are customarily used as described above. The pharmaceutical compositions are suitable for use in a variety of drug delivery systems. For a brief review of present methods for drug delivery, see Lancer, 1990, *Science* 249:1527-33 which is incorporated herein by reference.

The pharmaceutical preparations are preferably prepared and administered in dose units. Solid dose units are tablets, capsules or suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

Method of Screening Antagonists of Immunostimulatory DNA

In another aspect, the invention provides a method for screening compounds for their efficacy in inhibiting the immune response triggered by immunostimulatory DNA. Any compounds which are suitable for administration to subjects can be screened this way. In preferred embodiments, the compounds are selected from those having structures A and B, as described above.

This method initially involves a determination of the simulation of the immune response which is triggered by immunostimulatory DNA. The term "immune response" means either a humoral (antibody) or cellular (T lymphocyte) immune response. The "stimulation index" is a measure of a immunostimulatory DNA to affect an immune response which can be tested in various immune cell assays. The stimulation of the immune response can be assayed by measuring various immune parameters, e.g., measuring the antibody-forming capacity, number of lymphocyte subpopulations, mixed leukocyte response assay, and lymphocyte proliferation assay. The stimulation of the immune response can also be measured in an assay to measure resistance to infection or tumor growth. Methods for measuring a stimulation index are well known to those skilled in the art. For example, one assay is the incorporation of radioactive precursors, such as $^3$H labeled uridine or thymidine in a B-cell culture. The induction of secretion of a particular cytokine can also be used to assess the stimulation index. In general, methods known to those skilled in the art for detection of cell proliferation or viability of cells can be used in the present invention. Immunostimulatory DNA is contacted with a cell, thereby stimulating a measurable immune response. The inhibition of this immune response by the addition of a compound is then determined.

One particularly useful cell line for the assay of immunostimulatory DNA action is the mouse-mouse hybridoma plasma cell line 7TD1(ATTC #CRL 1851), which requires exoqenous IL-6 for growth, and has been used to characterize and assay IL-6 (Papadopolous et al., 1995. *J. Clin. Lab. Anal.* 9:234-7; Krakauer, 1993. *J. Immunoassay* 14:267-77). Growth of this cell line was not known to be supported by assents other than IL-6. Unexpectedly, it is found that immunostimulatory DNA can substitute for IL-6 in this cell line (Manzel et al., 1998. *Life Sciences* 62:23-7). Thus, the cell line 7TD1 is the first established cell line shown to be immunostimulatory DNA-dependent for growth.

An additional useful assay of antagonists of immunostimulatory DNA action is the protection by immunostimulatory DNA from the killing effect of antibody to cell surface immunoglobulin-M on WEHI 231 murine B-cells. Inhibition of this protection by the addition of a compound is then determined.

The invention will be further described in the following examples, which do not limit the scope of the invention described in the claims.

EXAMPLES

The following examples illustrate specific embodiments of the compounds of the invention, and demonstrate their efficacy in some aspects of the claimed methods. General procedures were employed as described here.

Unless otherwise noted, cell culture conditions were as follows. WEHI 231 cells (ATTC #CRL 1702) were grown in log phase in a medium of RPMI 1640 supplemented with 10% fetal bovine serum (heat inactivated at 65° C. for one hour), 0.3 grams/Liter of L-glutamine, 50 milligrams/Liter gentamycin, and 0.05 mM 2-mercaptoethanol in a 37° C. humid atmosphere with 5% $CO_2$. WEHI 231 cells were diluted with 0.4% trypan blue in phosphate-buffered saline (PBS) and live cells were counted in a hemocytometer chamber. Cells were resuspended in medium at $2 \times 10^5$/milliliter in 24-well tissue culture plates (Costar, Cambridge Mass.). Appropriate additions were made, and the cells were incubated and counted daily. WEHI 231 cells were diluted with fresh medium if the concentration exceeded $7 \times 10^5$/milliliter.

The 7TD1 cells were grown in RPMI 1640 supplemented with 10% fetal bovine serum (heat inactivated at 65° C., 1 hour), 0.3 grams/Liter L-glutamine, 50 milligrams/Liter gentamycin, 0.05 mM 2-mercaptoethanol, and 10 units per milliliter murine IL-6 in a 37° C. humid atmosphere with 5% $CO_2$. Viable 7TD1 cells were counted in a hemocytometer chamber in duplicate after dilution with 0.4% trypan blue. Cell counts were within 10% or 100 microliters of each other.

Preparation and sources of materials are as follows. For the production of IL-6 enzyme-linked immunosorbent assay (ELISA), cells were incubated as indicated, At 48 hours, the cell culture supernatant was harvested and assayed for murine IL-6 by ELISA according to manufacturer's instructions (PharMingen, San Diego Calif.). CpG-ODN 1760 has the sequence 5'-ATAMCGACGTTCAAGCAAG-3' synthesized on a phosphorothioate or (when indicated) on a phosphodiester backbone. The oligonucleotides were purchased from Genosys (The Woodlands TX). Murine IL-6, murine neutralizing antibody to IL-6, and ELISA antibodies were purchased from PharMingen (San Diego Calif.). The following compounds were all purchased from Sigma Chemical Co., St. Louis Mo; goat anti-mouse IgM ($\alpha$-sIgM, Cat. #M8644), lipopolysaccharide (*E. coli* serotype 0127:B8 Cat. #L3129), amodiaquine, chloroquine, quinacrine, primaquine, quinidine, quinine, coralyne chloride, and thapsigargin. Hydroxychloroquine was purchased from Copley Pharmaceutical, Inc., Canton Mass. Verapamil was from American Reagents Laboratory, Shirley N.Y. $C_2$-ceramide was purchased from Matreya, Inc., Pleasant Gap Pa. Acridine homodimer (bis-(6-chloro-2-methoxy-9-acridinyl)spermine) and 9-amino-6-chloro-2-methoxyacridine were purchased from Molecular Probes, Eugene Oreg.

The other compounds listed in Tables 2 and 3 were generous gifts from Dr. Jill Johnson of the National Cancer Institute. These compounds were synthesized generally according to known methods of synthesis (Elslager et al., 1969. *J. Med. Chem.* 12:970-4; Elslager et al. 1969. *J. Med. Chem.* 12:600-7; Marquez et al., 1972. *J. Med. Chem.* 36-9). The compounds are available from Developmental Therapeutics Program, National Cancer Institute, Executive Plaza North, Bethesda Md., 20892.

Example 1

Simultaneous Addition of Immunostimulatory DNA and Compounds

The assay of [$^3$H] Thymidine incorporation was carried out as follows. WEHI 231 cells (200 μL at 2×10$^5$/milliliter, in duplicate or triplicate) were incubated in a 96-well plate (Costar, Cambridge Mass.). Additions were made as indicated. After incubating for 16 hours, 0.5 μCi [methyl-$^3$H] thymidine (2 Ci/millimole, DuPont NEN, Boston Mass.) was added to each well, and the cells were incubated for another 4 hours. Cellular DNA was then captured onto glass fiber filters (Whatman 934AH) using a cell harvester (Brandel, Gaithersberg Md.). The filters were dried, placed into plastic scintillation vials with 10 milliliters of scintillation cocktail (EconoSafe, Research Products International, Mount Prospect Ill.), and counted in a liquid scintillation counter (Beckman LS-3133 T). The $^3$H recovered on the filter was expressed as a fraction of the $^3$H added. In a typical experiment, WEHI 231 cells incorporate about 15% of added $^3$H.

Figure 1:
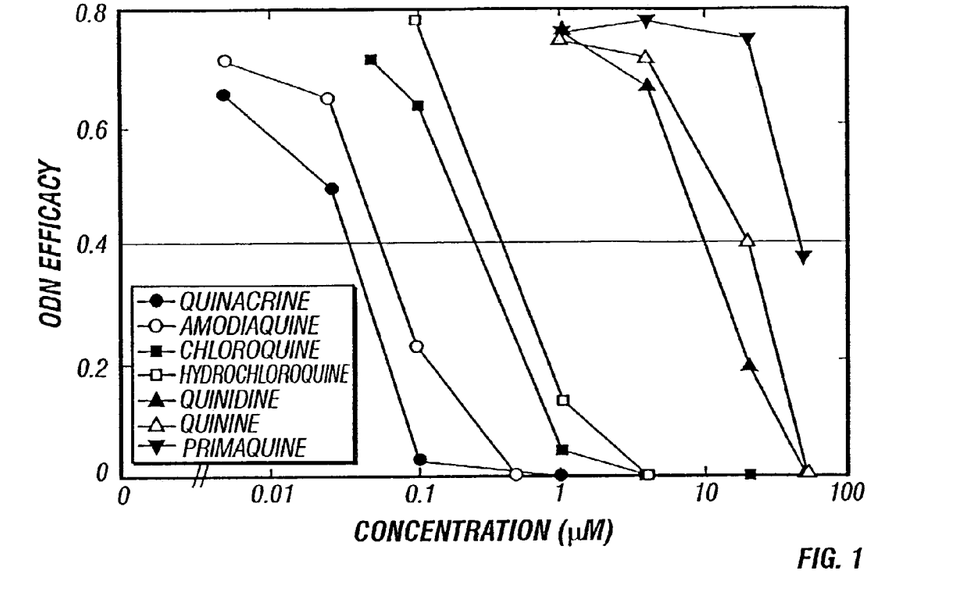
FIG. 1 is a graph showing the effect of various concentrations (log scale) of selected compounds (quinacrine, amodiaquine, chloroquine, hydroxychloroquine, quinidine, quinine, and primaquine) on ODN 1760 protection against the α-sIgM-induced inhibition of [$^3$H] thymidine uptake in WEHI 231 cells.

Referring to experiments summarized in FIG. 1, WEHI 231 cells (ca. 2×10$^5$ per milliliter) were incubated for 16 hours at 37° C. with 10 μgrams/milliliter α-sIgM, 6 μgrams/milliliter ODN 1760, and the indicated concentration of the compound. After 16 hours, 0.5 μCi [$^3$H] thymidine was added. After 4 more hours incubation, the cellular DNA was harvested onto glass fiber filters. The dry filters were counted in a liquid scintillation counter.

In the absence of other additions, cells incorporated about 20% of the added radioactivity. This was reduced to about 1% by the addition of α-sIgM. In the absence of a compound, ODN 1760 restored the uptake to about 15% of added radioactivity. The vertical axis of FIG. 1 shows the ratio of the uptake of cells incubated with α-sIgM divided by the uptake of cells incubated with α-sIgM with CpG-ODN, each measured with the indicated concentration of test compound. Each experimental point was the mean of at least duplicate measurements.

In the absence of other additions, α-sIgM powerfully inhibited [$^3$H] incorporation. This inhibition is almost completely relieved by ODN 1760. FIG. 1 shows that quinacrine, hydroxychloroquine, chloroquine and amodiaquine (substituted 4-aminochloroquinolines) completely inhibited the CpG-ODN effect at nanomolar concentrations. The compounds themselves did not inhibit [$^3$H] thymidine incorporation unless added at concentrations well in excess of 30 μM. Quinidine and quinine (substituted 4-methylquinolines) and primaquine (a substituted 8-aminoquinoline) had little effect on CpG-ODN action at concentrations less than 10 μM. Quinacrine and chloroquine showed promise as representative members of structural families useful in inhibiting immunostimulatory DNA-induced responses.

Example 2

Effect on Growth and Apoptosis

The DNA fragmentation assay was carried out generally as follows. WEHI 231 cells were incubated with 0.5 μCi/milliliter [$^3$H] thymidine for 3 hours, centrifuged, resuspended in 2 milliliters of fresh medium at 2×10$^5$/milliliter, and incubated in a 24-well plate with additions as indicated. After incubation for 16-18 hours, 1 milliliter aliquots of the cells were centrifuged, washed with 200 μliters PBS. This suspension was drawn into a pipette tip containing 25 μliters of 2% SDS, and the mixture was immediately ejected into a well of a 0.8% agarose TBE gel containing 0.5 μliter/milliliter ethidium bromide. The gel was electrophoresed for 1 hour at 65 volts, destained in water, and photographed under ultraviolet light. The lanes of the gel were cut into three approximately equal portions. The first portion included the gel well and the first 2 millimeters of the running lane. The second and third pieces were the remainder of the lane. The gel portions were melted in glass scintillation vials and mixed with a 20 milliliter of scintillation cocktail and counted in a scintillation counter. The amount of fragmented DNA (DNA in the second and third gel pieces) was expressed as a percentage of the total counts recovered in the lane.

Figure 2A:
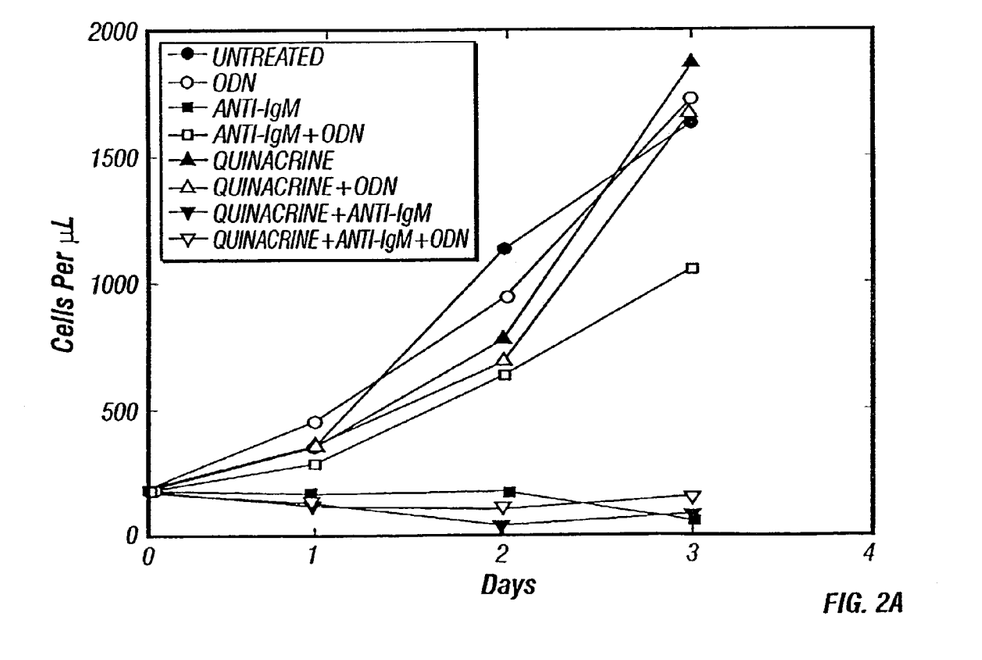
FIG. 2a is a graph showing the effect of various cell medium additives (ODN 1760. α-sIgM, ODN 1760/α-sIegM, quinacrine, quinacrine/ODN 1760, quinacrine/α-sIgM, and quinacrine/ODN 1760/α-sIgM) on the WEHI 231 cell count measured at different time periods after incubation.

Referring to the experiments summarized in FIG. 2a, WEHI 231 cells (2×10$^5$ per milliliter) were incubated with or without 6 μgrams/milliliter ODN 1760, 10 μgrams/milliliter α-sIgM, or 0.1 μM quinacrine as indicated. Live cells were counted daily. The cells were diluted in medium if their concentration exceeded 7×10$^5$ per milliliter. Referring to the experiments summarized in FIG. 2b, [$^3$H]-labeled WEHI 231 cells were incubated with no addition, or simultaneous additions as indicated. (α-sIgM 10 grams/milliliter, ODN 1760 6 μgrams/milliliter, quinacrine 0.1 μM). After 16 hours, cells were loaded into wells of 0.8% agarose gel by lysing with 1% SDS, and DNA electrophoresed 1 hour at 65 volts. The percentage fragmentation was estimated as described above. In this and other figures, error bars indicate 1 standard deviation.

Figure 2B:
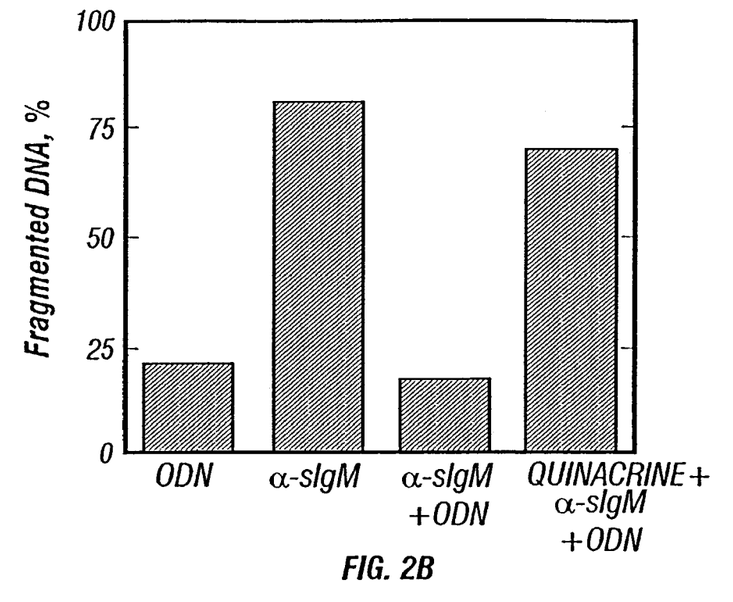
FIG. 2b is a bar graph showing the effect of various cell medium additives (ODN 1760, α-sIgM, ODN 1760/α-sIgM, and quinacrine/ODN 1760/α-sIgM) on the percentage of DNA fragmentation detected from WEHI 231 cells.

Quinacrine alone influenced neither cell growth nor cell death induced by α-sIgM. CpG-ODN protects cells against α-sIgM-induced apoptosis. Quinacrine reversed this protection by ODN 1760, revealed by measurement of both cell count over a period of three days (FIG. 2a) and percentage of fragmented DNA (FIG. 2b). Similar results were obtained with chloroquine. These data show that the effect of certain compounds on thymidine uptake is a true reflection of their effect on cell growth and protection from apoptosis.

Example 3

Effect on IL-6 Synthesis

The assay of IL6 was generally carried out as follows. WEHI cells (2×10$^5$/milliliter) were incubated with or without ODN 1760 (6 μgram/milliliter) and with or without chloroquine or quinacrine. After 24 hours, the IL-6 content of the supernatant was assayed by enzyme-linked immunoassay using two monoclonal antibodies in a sandwich technique as described by the manufacturer, using standards supplied (PharMingen, San Diego Calif.).

Besides inhibiting apoptosis, CpG-ODN stimulated the synthesis of cytokines, including IL-6. In the absence of other additions, WEHI 231 cell elaborated about 700 picograms IL-6 per milliliter. ODN 1760 increased this elaboration to over 10,000 picograms/milliliter. The addition of quinacrine (10 nM) or chloroquine (30 nM) completely reversed the effect of ODN 1760.

Example 4

Non-competitive Kinetics

Figure 3:
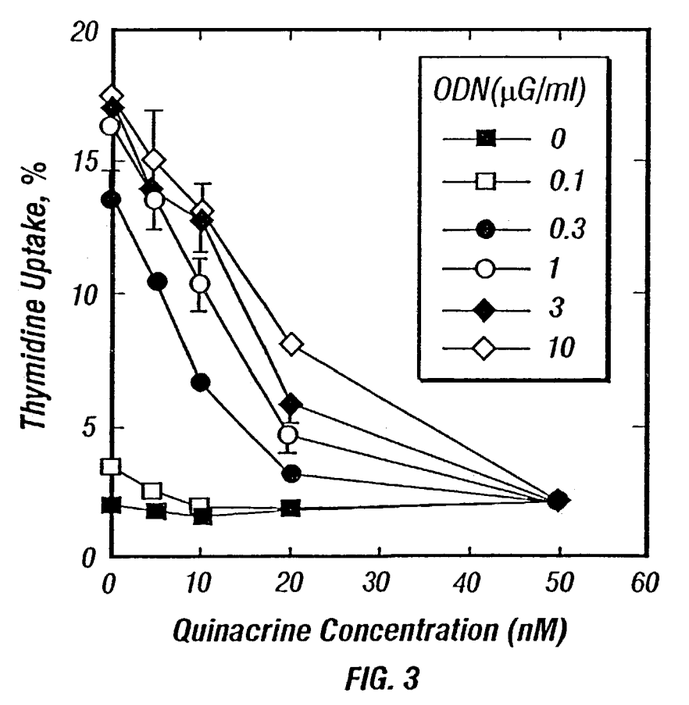
FIG. 3 is a graph showing the effect of various concentrations of ODN 1760 on the amount of [$^3$H] thymidine uptake in the presence of various concentrations of quinacrine in WEHI 231 cells treated with α-sIgM.

Referring to the experiments summarized in FIG. 3, 10 μgrams/milliliter α-sIgM and the indicated concentrations of ODN 1760 and quinacrine were added simultaneously to WEHI 231 cells. Thymidine incorporation was estimated at 16 hours as described for Example 1.

In the experiments summarized in FIG. 3, the inhibition by α-sIgM of [$^3$H] thymidine incorporation in the presence of a range of concentrations of ODN 1760 and quinacrine was measured. The data show that increasing the concentration of ODN 1760 did not overcome the inhibitory effect of quinacrine, suggesting that the compounds did not compete with immunostimulatory DNA for a common site, such as a receptor, an enzyme active site or a transport protein.

Example 5

Subsequent Addition

Figure 4:
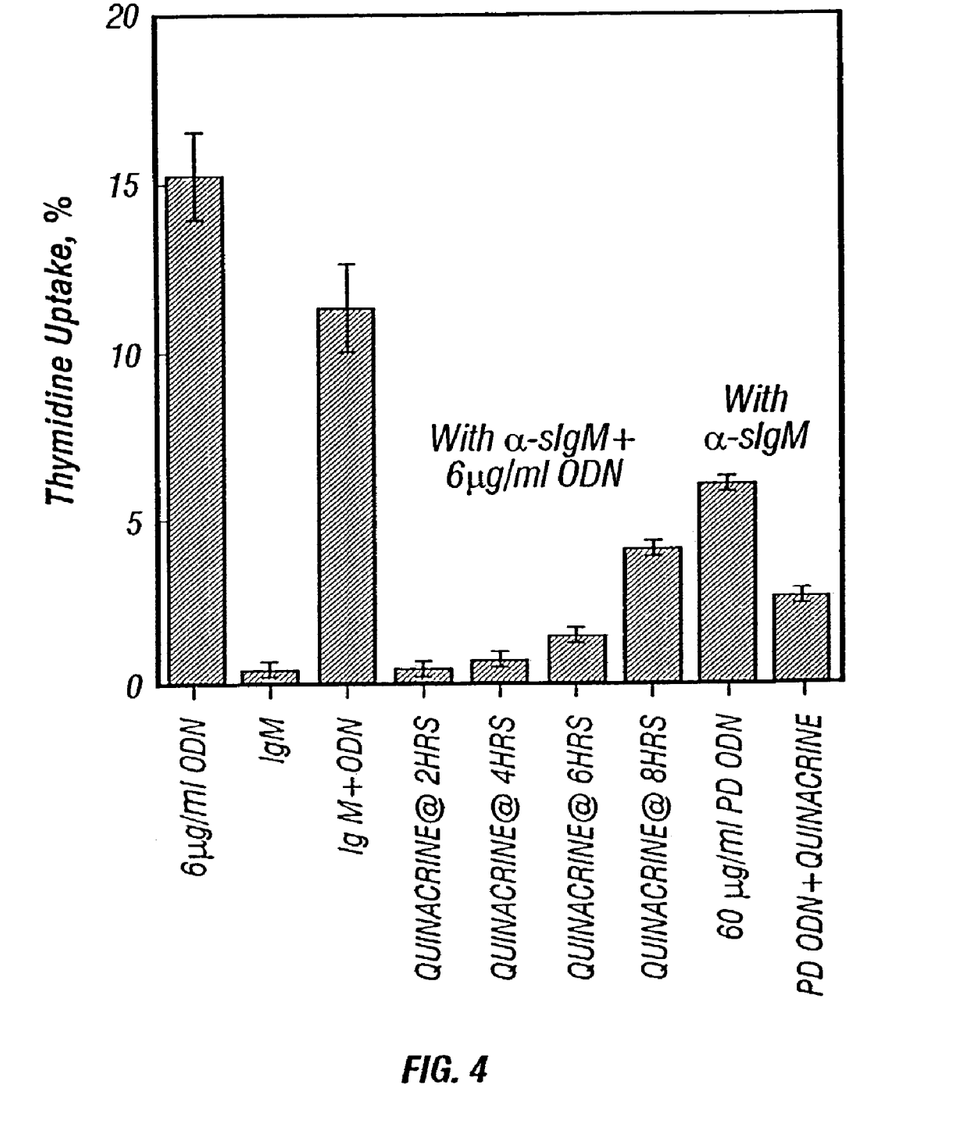
FIG. 4 is a bar graph showing the effect of additions of quinacrine at various times after incubation on the extent of [$^3$H] thymidine uptake in WEHI 231 cells treated with α-slim. Also displayed is a comparison of the effect on [$^3$H] thymidine uptake of incubation of α-sIgM-treated WEHI 231 cells with ODN 1760 and a phosphodiester ODN with the same sequence as ODN 1760.

Referring to the experiments summarized in FIG. 4, WEHI 231 cells were incubated with α-sIgM and ODN 1760. At times thereafter 0.1 μM quinacrine was added (data shown in the left three bars). Cells were incubated with 10 μgrams/milliliter (α-sIgM and ODN 1760 (6 μgrams/milliliter, phosphorothioate or a phosphodiester ODN with the same sequence as 1760 (PD ODN) (30 μM at time 0 hours and 8 hours; data represented in right six bars in FIG. 4). [$^3$H] thymidine incorporation was estimated at 16 hours.

It could be hypothesized that the compounds interfere with the transport of ODN to their intracellular site of action, in which case the compounds would prevent, but not reverse, the effect of nuclease-resistant CpG-ODN. This prediction did not appear to be correct. FIG. 4 shows that quinacrine blocked the action of CpG-ODN even when added 8 hours after the CpG-ODN, suggesting that quinacrine interfered with the mechanism the cell uses to recognize CpG-ODN (or with subsequent signal-response coupling), rather than transport.

CpG-ODN used in typical experiments was synthesized on a nuclease-resistant phosphorothioate backbone. The phosphodiester ODN with the same base sequence as ODN 1760 is considerably less potent than ODN 1760. FIG. 4 shows that quinacrine was effective in blocking the action of phosphodiester ODN, although the inhibitory effect was less complete than with phosphorothioate ODN.

Example 6

Effect of Quinacrine on Protection by Lipopolysaccharide

The B-cell repertoire is regulated by a number of factors that modulate clonal deletion, including lipopolysaccharides (endotoxin, LPS, derived from gram-negative bacteria), which promote B-cell growth and inhibit B-cell apoptosis. Chloroquine and other compounds have been reported to block LPS-induced responses in mononuclear cells (Jacobsen et al., 1995. *Trop. Med. Parasitol.* 46:8-92; Hannun, 1996. *Science* 274:1855-9).

Figure 5:
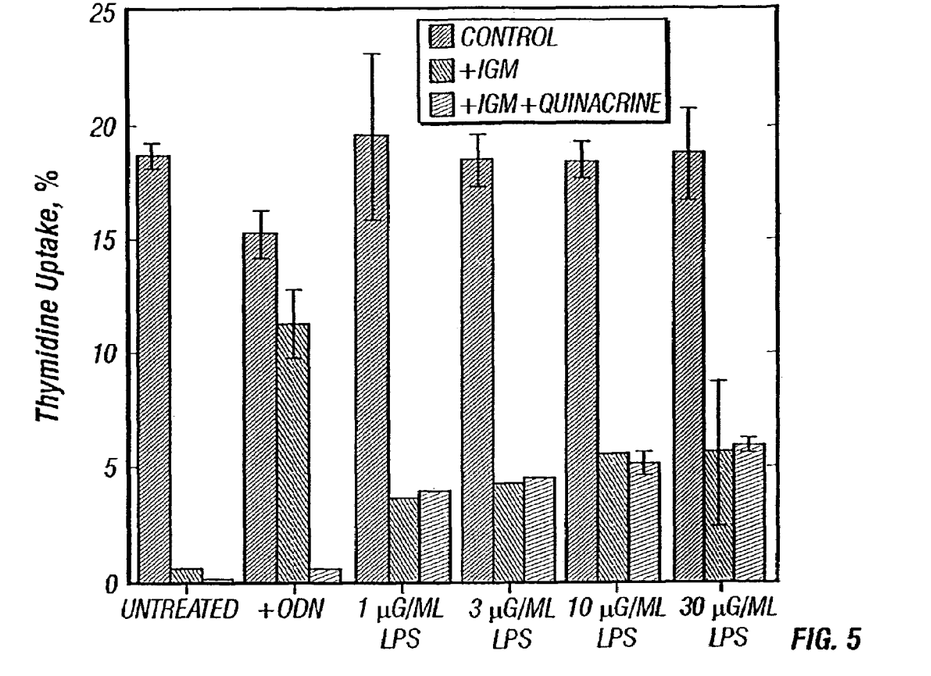
FIG. 5 is a bar graph showing the effect of quinacrine on the protection by lipopolysaccharides against α-sIgM-induced inhibition of [$^3$H] thymidine uptake by WEHI 231 cells.

In the experiments summarized in FIG. 5, the influence of LPS on α-sIgM-induced suppression of thymidine incorporation was examined. Even at high concentrations, LPS has much less ability than ODN 1760 to reverse α-sIgM-induced growth inhibition in WEHI 231 cells. Quinacrine at a concentration that completely reversed the effect of ODN 1760 had no effect on the action of LPS. Thus (at the concentration used) quinacrine did not block the detection of LPS and subsequent signal-response coupling in the same way that it did with CpG-ODN.

Lipopolysaccharide (LPS) was added at the indicated concentration with or without 10 μgrams/milliliter α-sIgM and 0.1 μM quinacrine. The small degree of protection against α-sIgM-induced inhibition of [$^3$H] thymidine uptake afforded by LPS is not influenced by quinacrine.

Example 7

Immunostimulatory DNA Blockade of Apoptosis Induced by Other Agents

CPG-ODN has been previously shown to block apoptosis in WEHI 231 cells which is induced by stimuli other than α-sIgM (Macfarlane et al., 1997. *Immunology* 91:586). The effect of quinacrine on the protection by ODN 1760 from cell death induced by agents other than α-sIgM was examined, to determine if the action of the studied compounds was restricted to α-sIgM-induced apoptosis. $C_2$-ceramide mediates receptor-induced cell death (Hannun, 1996. *Science* 274:1855-9) and inhibits thymidine incorporation. Thapsigargin induces an increase in intracellular calcium, resulting in massive DNA fragmentation.

Figure 6:
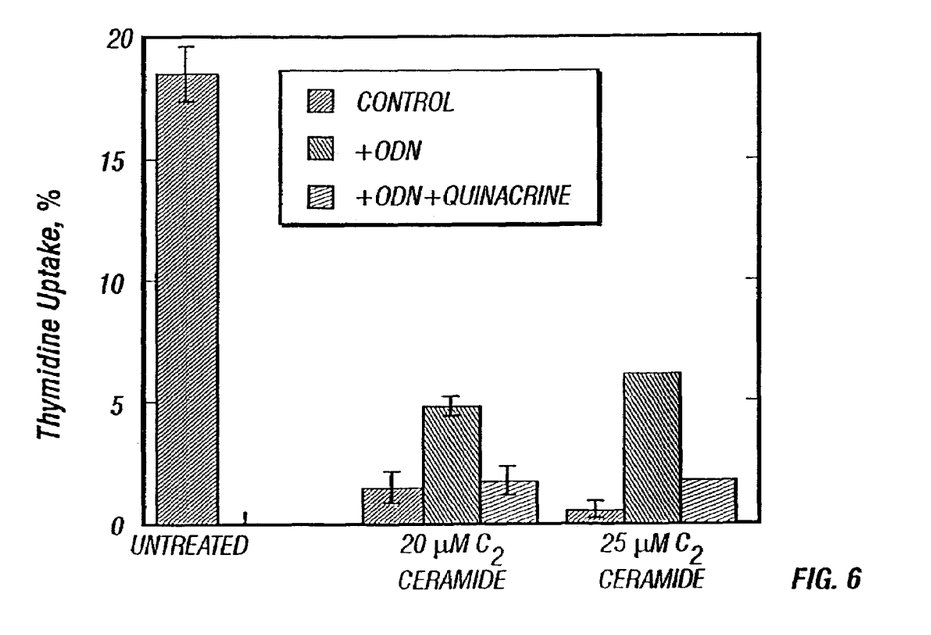
FIG. 6 is a bar graph showing the effect of quinacrine on the protection by ODN 1760 against $C_2$-ceramide-induced inhibition of [$^3$H] thymidine uptake in WEHI 231 cells.
Figure 7:
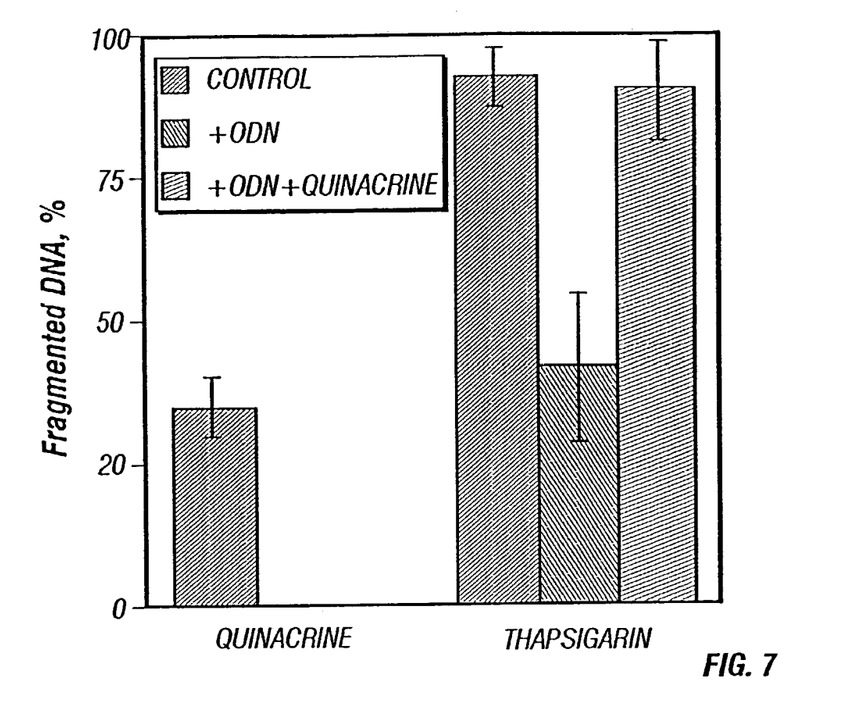
FIG. 7 is a bar graph showing the effect of quinacrine on the protection by ODN against thapsigargin-induced DNA fragmentation in WEHI 231 cells.

FIG. 6 shows that the effect of $C_2$-ceramide was reduced by ODN 1760, and that quinacrine blocked this protective effect. FIG. 7 shows that quinacrine also blocked the protective effect of ODN 1760 against thapsigargin-induced DNA fragmentation. Thus, quinacrine appeared to block the protective effect of immunostimulatory DNA generally, not just the protection against α-sIgM-induced apoptosis.

Referring to the experiments summarized in FIG. 6, WEHI 231 cells were incubated with $C_2$-ceramide as indicated with or without 6 μgrams/milliliter ODN and 0.1 μM quinacrine and thymidine incorporation was estimated. Referring to the experiments summarized in FIG. 7, WEHI 231 cells were prelabeled with 0.5 μCi/milliliter [$^3$H] thymidine for 3 hours, and resuspended in fresh medium containing 10 nM thapsigargin. 10 μgrams/milliliter α-sIgM, 6 μgrams/milliliter ODN, and/or 0.1 μM quinacrine as indicated. Cells were lysed 24 hours later, and the DNA was electrophoresed as described above in Example 2 to estimate the percentage fragmentation of DNA.

Example 8

Inhibition of 7TD1 Cell Growth by Compounds

Little growth occurs when 7TD1 cells are incubated in RPMI 1640 supplemented with fetal calf serum without added IL-6 or CpG-ODN. The addition of IL-6 supported vigorous growth with half-maximal effect at about 10 microliters/milliliter. The phosphorothioate CpG-ODN 1760 supported the growth of the 7TD1 cells in the absence of added IL-6. Growth stimulation by CpG-ODN was blocked by chloroquine and quinacrine, but these 4-aminoquinoline compounds had little effect on IL-6-induced growth (Table 1).

The 7TD1 cells were incubated for five days and were washed twice with medium to remove IL-6, and resuspended at $2 \times 10^4$ per milliliter in medium. Cell counts were performed and the percent inhibition of growth was computed. The term "anti" refers to 40 nanograms/milliliter neutralizing antibody to IL-6.

TABLE 1

Inhibition of 7TD1 cell growth

| Addition | 7TD1 cells/μL | % Growth Inhibition |
|---|---|---|
| no addition | 10 | |
| 10 μg/mL IL-6 | 887 | (0) |
| 10 μg/mL IL-6 + anti + IL-6 | 117 | 86.7 |
| 10 μg/mL IL-6 + 1 μM chloroquine | 610 | 31.2 |
| 10 μg/mL IL-6 + 3 μM chloroquine | 547 | 38.3 |
| 10 μg/mL IL-6 + 0.1 μM quinacrine | 707 | 20.2 |
| 10 μg/mL IL-6 + 0.3 μM quinacrine | 595 | 32.9 |
| 10 μg/mL IL-6 + 1 μM quinacrine | 587 | 33.8 |
| 6 μg/mL ODN 1760 | 407 | (0) |
| 6 μg/mL ODN 1760 + anti + IL6 | 365 | 10.4 |
| 6 μg/mL ODN 1760 + 1 μg chloroquine | 7 | 98.1 |
| 6 μg/mL ODN 1760 + 3μ chloroquine | 10 | 97.5 |
| 6 μg/mL ODN 1760 0.1 μM quincrine | 20 | 95 |
| 6 μg/mL ODN 1760 0.3 μM quincrine | 20 | 95 |
| 6 μg/mL ODN 1760 1 μM quincrine | 15 | 96.3 |

Example 9

Immunostimulatory Effects on Human Mononuclear Cells

The effects of the compounds is not restricted to immortal mouse cells. Unfractionated human peripheral blood cells incorporated thymidine and produced IL-6 when exposed to ODN 1760, as displayed in FIGS. 8 and 9, respectively. Both effects were inhibited by quinacrine and chloroquine.

Figure 8:
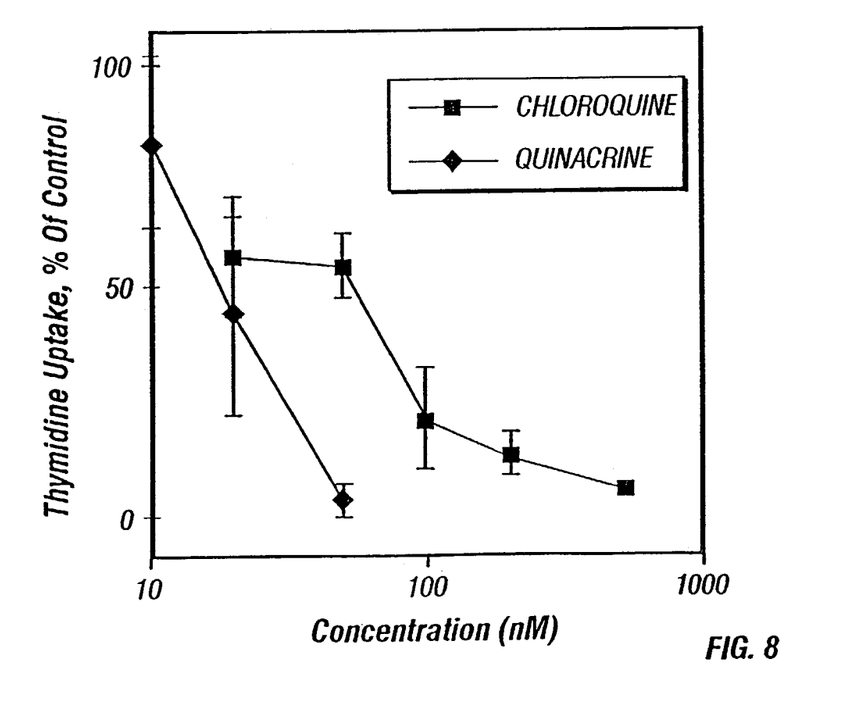
FIG. 8 is a graph showing ODN 1760-induced effects on percentage of [$^3$H] thymidine uptake in human mononuclear cells.

Referring, to the experiments summarized in FIG. 8, human mononuclear cells ($2 \times 10^6$/milliliter) from three different donors were incubated with or without ODN 1760 and the indicated concentration of quinacrine or chloroquine for four days. [$^3$H] thymidine incorporation (18 hour pulse) was then measured. FIG. 8 shows $^3$H uptake as a percentage of ODN-treated cells. The $^3$H uptake per donor for control samples was as follows: donor 1, 4.31%, donor 2, 2.76%; donor 3, 6.39%. Thymidine incorporation for untreated samples was less than 0.05%. Samples from three donors were averaged, and error bars indicate 1 standard deviation.

Figure 9:
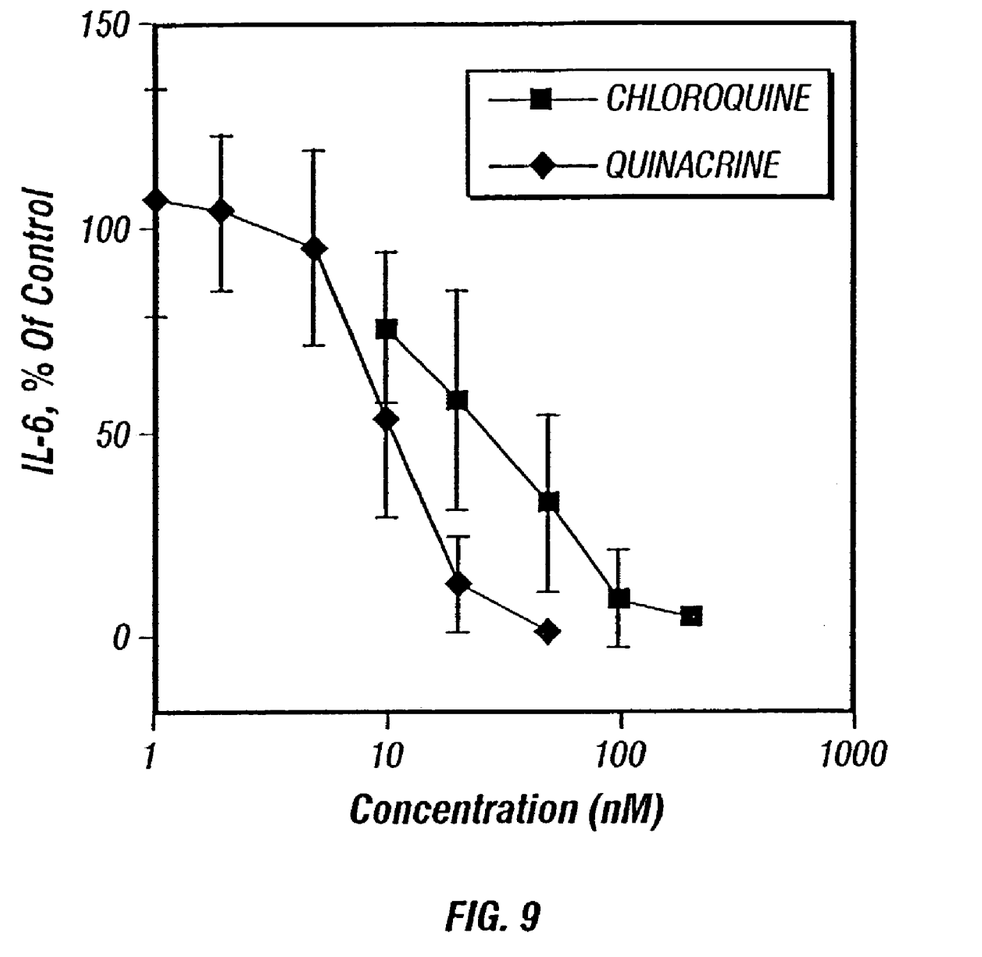
FIG. 9 is a graph showing ODN 1760-induced effects on percentage of IL-6 production in human mononuclear cells.

Referring to the experiments summarized in FIG. 9, human peripheral blood mononuclear cells (PBMC) from three donors were incubated with or without ODN 1760 and the indicated concentration of test compound. After 24 hours, the concentration of IL-6 was determined in the supernatant. The figure indicates the percentage of IL-6 in reference to ODN-treated cells. The IL-6 amounts for control sample per donor were as follows: donor 1, 203 picograms/milliliter; donor 2, 71.5 picograms/milliliter; donor 3, 465 picograms/milliliter. IL-6 measured from untreated cells was 0-21 picograms/milliliter. Results from the three donors were averaged, and error bars indicate 1 standard deviation.

Example 10

9-Aminoacridines and 4-Aminoquinoline Derivatives

Some specific embodiments of 4-aminoquinolines useful in the methods of the invention are included in Table 2. Some specific embodiments of 9-aminoacridines useful in the methods of the invention are included in Table 3.

The structures are listed as changes from quinacrine or chloroquine. The symbol — indicates no change. Me and Et indicate —CH$_3$ and —CH$_2$CH$_3$ respectively. Aromatic substituents are in the para position except as indicated. The activity is —log$_{10}$ of the concentration (M) required for half maximal inhibition of CpG-ODN effect on [$^3$H] thymidine uptake in the presence of α-sIgM. The last column is the activity expressed as a fraction of activity of chloroquine (fold).

TABLE 2

| Cmpd.# | R2 | R3 | R5 | R6 | R7 | R8 | R4 sidechain | Activity | Fold |
|---|---|---|---|---|---|---|---|---|---|
|  | H | H | H | H | Cl | H | NHCHMe(CH$_2$)$_3$NEt$_2$ | 6.96 | 1.00 |
| 34 | — | — | — | — | — | — | NHCH$_2$CH(C$_6$H$_4$OMe)(CH$_2$)NEt$_2$ | 7.66 | 5.04 |
| 43 | — | — | — | SCH$_2$C$_6$H$_5$ | — | — |  | 7.62 | 4.57 |
| 44 | C$_6$H$_5$ | — | — | — | OMe | — |  | 7.52 | 3.63 |
| 33 | — | — | — | — | — | — | NHCH$_2$CH(C$_6$H$_4$Cl)(CH$_2$)$_3$NEt$_2$ | 7.43 | 2.95 |
| 69 | C(Me)—C | — | — | NMe$_2$ | H | — | — | 7.42 | 2.88 |
| 32 | — | Me | — | Me | — | — | — | 7.37 | 2.57 |
| 48 | C$_6$H$_5$ | — | — | — | — | — | — | 7.29 | 2.14 |
| 51 | — | — | — | C$_6$H$_5$ | H | — | — | 7.17 | 1.62 |
| 60 | — | Me | — | — | — | — | NH(CH$_2$)$_4$N(C$_4$H$_2$)$_2$ | 7.15 | 1.55 |
| 42 | — | — | — | OC$_6$H$_5$ | H | — | — | 7.13 | 1.48 |
| 56 | — | — | — | — | — | — | NHCH(CH$_2$Cl)CH$_2$)$_3$NEt$_2$ | 7.12 | 1.45 |
| 7 | — | — | — | — | — | — | NHCH$_2$CH(C$_6$H$_5$)(CH$_2$)$_2$NEt$_2$ | 7.10 | 1.38 |
| 18 | — | — | — | — | — | — | NHC$_6$H$_3$pOHmNEt$_2$ | 7.00 | 1.10 |
| 15 | — | — | — | — | — | — | — | 6.96 | 1.00 |
| 36 | — | Me | — | — | — | — | NHCH$_2$(C$_6$H$_5$)(CH$_2$)$_2$NEt$_2$ | 6.94 | 0.95 |
| 35 | — | Me | — | — | — | — | NH(CH$_2$)$_4$NEt | 6.87 | 0.81 |
| 53 | — | — | — | — | — | — | NHCHMeCH—CHCH$_2$NEt | 6.87 | 0.81 |
| 68 | — | — | — | — | — | — | NH(CH$_2$)$_3$C(Me)$_2$NMe$_2$ | 6.87 | 0.81 |
| 61 | — | — | — | — | — | — | NHCH$_2$CH(C$_6$H$_4$OMe)(CH$_2$)$_2$NEt$_2$ | 6.86 | 0.79 |
| 9 | — | — | Cl | — | H | — | — | 6.84 | 0.76 |
| 50 | — | — | — | — | OC$_6$H$_5$ | — | — | 6.83 | 0.74 |
| 4 | — | — | — | — | Br | — | — | 6.82 | 0.72 |
| 10 | — | — | — | — | — | — | NH(CH$_2$)$_4$NME$_2$ | 6.82 | 0.72 |
| 12 | — | C$_6$H$_5$ | — | — | — | — | — | 6.80 | 0.69 |
| 64 | — | — | — | — | OC$_6$H$_5$ | — | — | 6.75 | 0.62 |
| 65 | — | Me | — | — | — | — | NHCHCH(C$_6$H$_3$m.pCl$_2$)(CH$_2$)$_2$NEt$_2$ | 6.72 | 0.58 |

TABLE 2-continued

| Cmpd.# | R2 | R3 | R5 | R6 | R7 | R8 | R4 sidechain | Activity | Fold |
|---|---|---|---|---|---|---|---|---|---|
| 1 | — | Me | — | — | — | — | — | 6.70 | 0.55 |
| 67 | — | — | — | — | — | — | $NH(CH_2)_2CH(OH)CH_2NEt_2$ | 6.68 | 0.52 |
| 41 | — | Me | — | — | Ome | — | — | 6.64 | 0.28 |
| 11 | — | — | — | — | — | — | — | 6.56 | 0.40 |
| 62 | — | Me | Br | — | H | — | — | 6.51 | 0.35 |
| 16 | — | — | — | — | — | — | $NHCH(CH_3)(CH_2)_3NEtEtOH$ | 6.39 | 0.27 |
| 13 | — | — | — | — | F | — | — | 6.38 | 0.26 |
| 40 | — | Me | Me | — | H | — | — | 6.32 | 0.23 |
| 46 | — | Me | — | Me | — | — | — | 6.28 | 0.21 |
| 14 | — | — | — | — | Ome | — | — | 6.20 | 0.17 |
| 3 | — | — | — | — | Me | — | — | 6.16 | 0.16 |
| 63 | — | Me | — | — | — | OMe | — | 5.95 | 0.10 |
| 71 | — | Me | — | OEt | — | — | — | 5.90 | 0.09 |
| 45 | — | — | — | — | — | — | $NCH_2CH(C_6H_4OH)(CH_2)_2NEt$ | 5.76 | 0.06 |
| 39 | Me | Me | — | — | H | — | — | 5.58 | 0.04 |
| 37 | — | — | — | — | Me | — | — | 5.50 | 0.03 |
| 47 | — | — | — | — | — | — | Ncyclopentane2-OH | 5.25 | 0.02 |
| 8 | — | — | — | — | — | — | $NCHMe(CH_2)_3N^1CH_3Et_2$ | 5.18 | 0.02 |
| 2 | — | — | — | — | — | — | $CH_2NHCHMe(CH_2)Net_2$ | 5.00 | 0.01 |

TABLE 3

| Cmpd.# | R1 | R2 | R3 | R5 | R6 | R7 | R8 | R9 sidechain | Activity, -$\log_{10}$ | vs. Chloroquine, fold |
|---|---|---|---|---|---|---|---|---|---|---|
| quinacrine | H | Ome | H | H | Cl | H | H | $NHCHMe(CH_2)_3NEt_2$ | 7.85 | 7.76 |
| 26 | — | — | Ome | — | — | — | — | — | 7.99 | 10.72 |
| 25 | — | — | — | — | — | — | — | $NHCHC_6H_5(CH_2)_3NEt_2$ | 7.72 | 5.75 |
| 24 | — | — | — | — | — | — | — | $NHCH(3\text{-pyridyl})(CH_2)_3NEt_2$ | 7.52 | 3.63 |
| 23 | — | — | — | — | — | — | — | $NHCH(C_6H_4F)(CH_2)_3NEt_2$ | 7.37 | 2.57 |
| 30 | — | — | — | — | — | — | — | $NHCH(C_6H_4OMe)(CH_2)_3NEt_2$ | 7.28 | 2.09 |
| 29 | — | — | — | — | — | — | — | $NHCH(1\text{-naphthyl})(CH_2)_3NEt_2$ | 7.24 | 1.91 |
| 27 | — | — | — | — | — | — | — | $NHCH(2\text{-thienyl})(CH_2)_3NEt_2$ | 7.22 | 1.82 |
| 28 | — | — | — | — | — | — | — | $NHCH(C_6H_4Cl)(CH_2)_3NEt_2$ | 7.22 | 1.82 |
| 59 | — | — | — | — | — | — | — | $NH_2$ | 6.96 | 1.00 |
| 58 | — | Aciidine homodimer | — | — | — | — | — | — | 6.38 | 0.26 |

---

What is claimed is:

1. A method of identifying a compound that inhibits an immunostimulatory DNA-induced response, the method comprising contacting a cell with an immunostimulatory DNA, thereby inducing a measurable immune response, and a test compound and detecting inhibition of the immunostimulatory effect of the immunostimulatory DNA, wherein the test compound is selected from the group consisting of: compounds, other than chloroquine, having the structural formula:

compounds having the structural formula:

wherein
$R_A$ is a hydrogen atom, a lower alkyl group, or linked to $R_B$ by a substituted or unsubstituted alkyl chain;
$R_B$ is a hydrogen atom, an alicyclic group, an alkyl secondary, tertiary or quarternary amine, or an alkenyl secondary, tertiary or quarternary amine;
$R_2$ is a hydrogen atom, a lower alkyl group, an aryl group, a heteroaromatic group, or a lower alkenyl group substituted with an aryl group;
$R_3$ is a hydrogen atom, a lower alkyl group, or an aromatic group;
$R_5$ is a hydrogen atom, a lower alkyl group, or a halogen atom;
$R_6$ is a hydrogen atom, a lower alkyl group, a lower alkoxy group, an aryloxy group, an aryl group, an amino group or a thioether group;
$R_7$ is a hydrogen atom, a lower alkyl group, a lower alkoxy group, an aryloxy group, a haloalkyl group, or a halogen atom; and
$R_8$ is a hydrogen atom, or a lower alkoxy group, and pharmaceutically acceptable salts thereof, with the proviso that if $R_7$ is a halogen, then at least one of $R_2$, $R_3$, $R_5$, $R_6$ or $R_8$ is non-hydrogen and $R_B$ is not 4-[N,N-dialkyl-n-pentylamine] or 4-[N-alkyl-N-hydroxyalkyl-n-pentylamine], wherein
$R_B$ is a hydrogen atom, or an alkyl secondary or tertiary amino substitutent selected from the group consisting of 2-[N,N-dimethyl ethylamine], 2-[N-methyl ethylamine], 2-[ethyl-N,N-dialkyl amine], 2-[ethyl-N-alkyl amine], 2-[ethyl amine], 3-[propyl-N,N-dialkyl amine], 3-[propyl-N-alkyl amine], 4-[pentyl-N,N-dialkyl amine], 4-[pentyl-N-alkyl amine], 4-[pentyl amine], 4-[butyl-N,N-dialkyl amine], 4-[butyl-N-alkyl amine], 4-[butyl amine], 4-[N,N-diethyl pentylamine], 4-[N,N-diethyl butylamine], 4-[4-aryl-N,N-dialkyl butylamine], 4-[4-heteroaromatic-N,N-dialkyl butylamine], 4-[4-aryl-N-alkyl butylamine], 4-[4-heteroaromatic-N-alkyl butylamine], 4-[N,N-dialkyl pentylamine], and 7-[hepta-4-methyl-4-azaamine];
$R_2$ is a lower alkyl group;
$R_3$ is a hydrogen atom or a lower alkoxy group; and
X is a halogen atom, and pharmaceutically acceptable salts thereof.

2. The method of claim 1, wherein the cell is a hybridoma plasma cell.

3. The method of claim 1, wherein the detecting is by measuring IL-6 production.

4. The method of claim 2, wherein the hybridoma plasma cell is 7TD1.

* * * * *

UNITED STATES PATENT AND TRADEMARK OFFICE
CERTIFICATE OF CORRECTION

PATENT NO. : 7,354,711 B2  Page 1 of 1
APPLICATION NO. : 10/336635
DATED : April 8, 2008
INVENTOR(S) : Donald E. Macfarlane It is certified that error appears in the above-identified patent and that said Letters Patent is hereby corrected as shown below:

At columns 19-20, Table 3, last line , "Aciidine homodimer" should read --Acridine homodimer--.

At column 21, line 17, Claim 1, "quarternary" should read --quaternary--.

At column 21, line 18, Claim 1, "quarternary" should read --quaternary--.

Signed and Sealed this

Fifteenth Day of July, 2008

JON W. DUDAS
*Director of the United States Patent and Trademark Office*

SEQUENCE LISTING

```
<160> NUMBER OF SEQ ID NOS: 1
<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ataatcgacg ttcaagcaag                                                    20
```